(12) United States Patent
Pan et al.

(10) Patent No.: US 11,064,933 B2
(45) Date of Patent: Jul. 20, 2021

(54) METHOD OF NORMALIZING TACHYCARDIA ECG BASED ON P-WAVE AND T-WAVE DATA INTERPOLATION

(71) Applicant: Industry-Academic Cooperation Foundation, Chosun University, Gwangju (KR)

(72) Inventors: Sung Bum Pan, Gwangju (KR); Gyu Ho Choi, Gwangju (KR)

(73) Assignee: Industry-Academic Cooperation Foundation, Chosun University, Gwangju (KR)

( * ) Notice: Subject to any disclaimer, the term of this patent is extended or adjusted under 35 U.S.C. 154(b) by 4 days.

(21) Appl. No.: 16/786,859

(22) Filed: Feb. 10, 2020

(65) Prior Publication Data
US 2021/0169360 A1 Jun. 10, 2021

(30) Foreign Application Priority Data
Dec. 6, 2019 (KR) .......................... 10-2019-0161933

(51) Int. Cl.
*A61B 5/363* (2021.01)
*A61B 5/316* (2021.01)

(52) U.S. Cl.
CPC .............. *A61B 5/363* (2021.01); *A61B 5/316* (2021.01)

(58) Field of Classification Search
CPC ................................ A61B 5/363; A61B 5/316
See application file for complete search history.

(56) References Cited

U.S. PATENT DOCUMENTS

| 2009/0076402 | A1* | 3/2009 | Hoium .................... A61B 5/726 600/515 |
| 2012/0165690 | A1* | 6/2012 | Chen ..................... A61B 5/7207 600/509 |
| 2016/0256063 | A1* | 9/2016 | Friedman ........... A61B 5/02455 |
| 2017/0071507 | A1* | 3/2017 | Fernando ............... A61B 5/332 |
| 2018/0168472 | A1* | 6/2018 | Pan ........................ A61B 5/352 |
| 2019/0076044 | A1* | 3/2019 | Krubsack ............... A61B 5/339 |

* cited by examiner

*Primary Examiner* — Catherine M Voorhees
(74) *Attorney, Agent, or Firm* — Studebaker & Brackett PC

(57) ABSTRACT

The present disclosure relates to a method of normalizing a tachycardia electrocardiogram (ECG) on the basis of P-wave and T-wave data interpolation. The method of normalizing a tachycardia ECG on the basis of P-wave and T-wave data interpolation includes (a) receiving a first ECG signal from a subject, (b) detecting P-wave and T-wave peaks in the received first ECG signal, (c) segmenting the received first ECG signal into one-cycle ECG signals on the basis of the detected P-wave and T-wave peaks, (d) segmenting the one-cycle ECG signals into a P-wave period, a QRS complex period, and a T-wave period, and (e) normalizing the segmented P-wave and T-wave periods through data interpolation.

11 Claims, 8 Drawing Sheets

FIG. 9

Ⓐ EUCLIDEAN DISTANCE CALCULATION RESULT REGARDING GENERAL STATE 1
Ⓑ EUCLIDEAN DISTANCE CALCULATION RESULT REGARDING PRE-EXERCISE AND MID-EXERCISE STATES 1 AND 6
Ⓒ EUCLIDEAN DISTANCE CALCULATION RESULT REGARDING MID-EXERCISE AND POST-EXERCISE STATES 6 AND 7
Ⓓ EUCLIDEAN DISTANCE CALCULATION RESULT REGARDING PRE-EXERCISE AND POST EXERCISE STATES 1 AND 7

| SUBJECT | | SUBJECT NUMBER 5 | | | | | | | |
|---|---|---|---|---|---|---|---|---|---|
| | | Ⓐ | | Ⓑ | | Ⓒ | | Ⓓ | |
| NORMALIZED OR NOT | | X | ○ | X | ○ | X | ○ | X | ○ |
| ECG CYCLE | 5 | 0.3777 | 0.4176 | 1.1326 | 0.5666 | 1.4489 | 0.4139 | 0.8827 | 0.4196 |
| | 10 | 0.2435 | 0.1684 | 1.1352 | 0.5582 | 1.4643 | 0.4456 | 0.9622 | 0.5438 |
| | 15 | 0.2529 | 0.2150 | 1.0637 | 0.4742 | 1.4657 | 0.4516 | 1.0010 | 0.5296 |
| | 20 | 0.3549 | 0.3292 | 1.0364 | 0.5430 | 1.6043 | 0.4712 | 1.1362 | 0.5432 |
| | 25 | 0.1863 | 0.1722 | 1.1583 | 0.4183 | 1.6259 | 0.5170 | 1.1159 | 0.5328 |
| | 30 | 0.3207 | 0.2888 | 1.1892 | 0.5852 | 1.4440 | 0.5129 | 0.9384 | 0.5246 |
| AVERAGE | | 0.2893 | | | | | | | |
| | | | 0.2652 | | | | | | |
| | | | | 1.1192 | | | | | |
| | | | | | 0.5243 | | | | |
| | | | | | | 1.5089 | | | |
| | | | | | | | 0.4687 | | |
| | | | | | | | | 1.0061 | |
| | | | | | | | | | 0.5156 |
| 20 SUBJECTS | | ⋮ | ⋮ | ⋮ | ⋮ | ⋮ | ⋮ | ⋮ | ⋮ |
| OVERALL AVERAGE | | 0.2057 | 0.2032 | 0.6379 | 0.6070 | 0.6303 | 0.5163 | 0.5247 | 0.4014 |
| SIMILARITY VARIATION | | 1.2% INCREASE | | 4.8% INCREASE | | 18.1% INCREASE | | 23.5% INCREASE | |

METHOD OF NORMALIZING TACHYCARDIA ECG BASED ON P-WAVE AND T-WAVE DATA INTERPOLATION

CROSS-REFERENCE TO RELATED APPLICATION

This application claims priority to and the benefit of Korean Patent Application No. 10-2019-0161933, filed on Dec. 6, 2019, the disclosure of which is incorporated herein by reference in its entirety.

BACKGROUND

1. Field of the Invention

The present invention relates to a method of normalizing a tachycardia electrocardiogram (ECG) on the basis of P-wave and T-wave data interpolation and more particularly, to a method of normalizing a tachycardia ECG according to general pre-exercise ECG cycles by interpolating P-wave and T-wave data of a tachycardia ECG.

2. Discussion of Related Art

When the heart beats, a minute potential difference occurs in the myocardium. An electrocardiogram (ECG) refers to a graph obtained by measuring the minute potential difference through electrodes attached to a living body surface and recording the variation curve according to time.

The waveform of an ECG basically includes a P wave, a QRS complex, and a T wave. The P wave is generated when the atria are depolarized, the QRS complex is generated when the ventricles are depolarized, and the T wave is generated when the ventricles are repolarized.

Since an ECG is generated from an electrical signal of the heart, ECG signals of individuals may be differently measured according to measurement environments, such as unique cardiac characteristics or behavioristic characteristics, of the subjects whose ECGs are measured. In particular, a post-exercise ECG does not correspond to a pre-exercise ECG due to tachycardia which occurs temporally. For this reason, the performance of recognizing an ECG may be degraded.

To solve this problem, a post-exercise ECG is normalized into a pre-exercise ECG through frequency filtering, or one whole cycle or a specific period is resampled. However, P waves, QRS complexes, and T waves are distorted in the case of frequency filtering, and the position of a QRS complex period is not fixed in the case of resampling.

SUMMARY OF THE INVENTION

The present invention is directed to providing a method of normalizing a tachycardia electrocardiogram (ECG) on the basis of P-wave and T-wave data interpolation by which one tachycardia ECG cycle is normalized according to a general pre-exercise ECG cycle through data interpolation.

The present invention is also directed to providing a method of normalizing a tachycardia ECG on the basis of P-wave and T-wave data interpolation by which P waves, QRS complexes, and T waves are not distorted and QRS complex periods are fixed.

Objects of the present invention are not limited to those described above, and other objects which are not mentioned will be apparent from the following descriptions.

According to an exemplary embodiment of the present invention, a method of normalizing a tachycardia ECG on the basis of P-wave and T-wave data interpolation includes (a) receiving a first ECG signal from a subject, (b) detecting P-wave and T-wave peaks in the received first ECG signal, (c) segmenting the received first ECG signal into a one-cycle ECG signal on the basis of the detected P-wave and T-wave peaks, (d) segmenting the one-cycle ECG signal into a P-wave period, a QRS complex period, and a T-wave period, and (e) normalizing the segmented P-wave and T-wave periods through data interpolation.

The method may further include, before operation (a), receiving a second ECG signal from the subject.

Operation (e) may include normalizing the segmented P-wave and T-wave periods according to a cycle of the second ECG signal through data interpolation.

Operation (b) may include (b-1) detecting an R-wave peak in the received first ECG signal and (b-2) detecting the P-wave and T-wave peaks in the received first ECG signal on the basis of a position of the detected R-wave peak.

Operation (b-1) may include detecting the R-wave peak by using a Pan-Tomkins algorithm. Operation (b-2) may include detecting a peak in a preset period on a left side of the R-wave peak as the P-wave peak and detecting a peak in a preset period on a right side of the R-wave peaks as the T-wave peak.

Operation (c) may include segmenting the received first ECG signal into the one-cycle ECG signal on the basis of a preset position on a left side of the P-wave peak and a preset position on a right side of the T-wave peak.

Operation (d) may include segmenting the one-cycle ECG signal into the QRS complex period on the basis of preset positions on a left side and a right side of the R-wave peak.

Operation (e) may include, when sizes of the P-wave and T-wave periods of the first ECG signal are respectively smaller than sizes of P-wave and T-wave periods of the second ECG signal, normalizing the P-wave and T-wave periods through data interpolation.

The method may further include, after operation (e), combining the P-wave and T-wave periods, of which data has been interpolated, with the QRS complex period.

According to another exemplary embodiment of the present invention, a computer-readable recording medium may store a program for executing the method in a computer.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which:

FIG. 9 is a table showing results of measuring similarity in an experimental example.

DETAILED DESCRIPTION OF EXEMPLARY EMBODIMENTS

Figure 1:
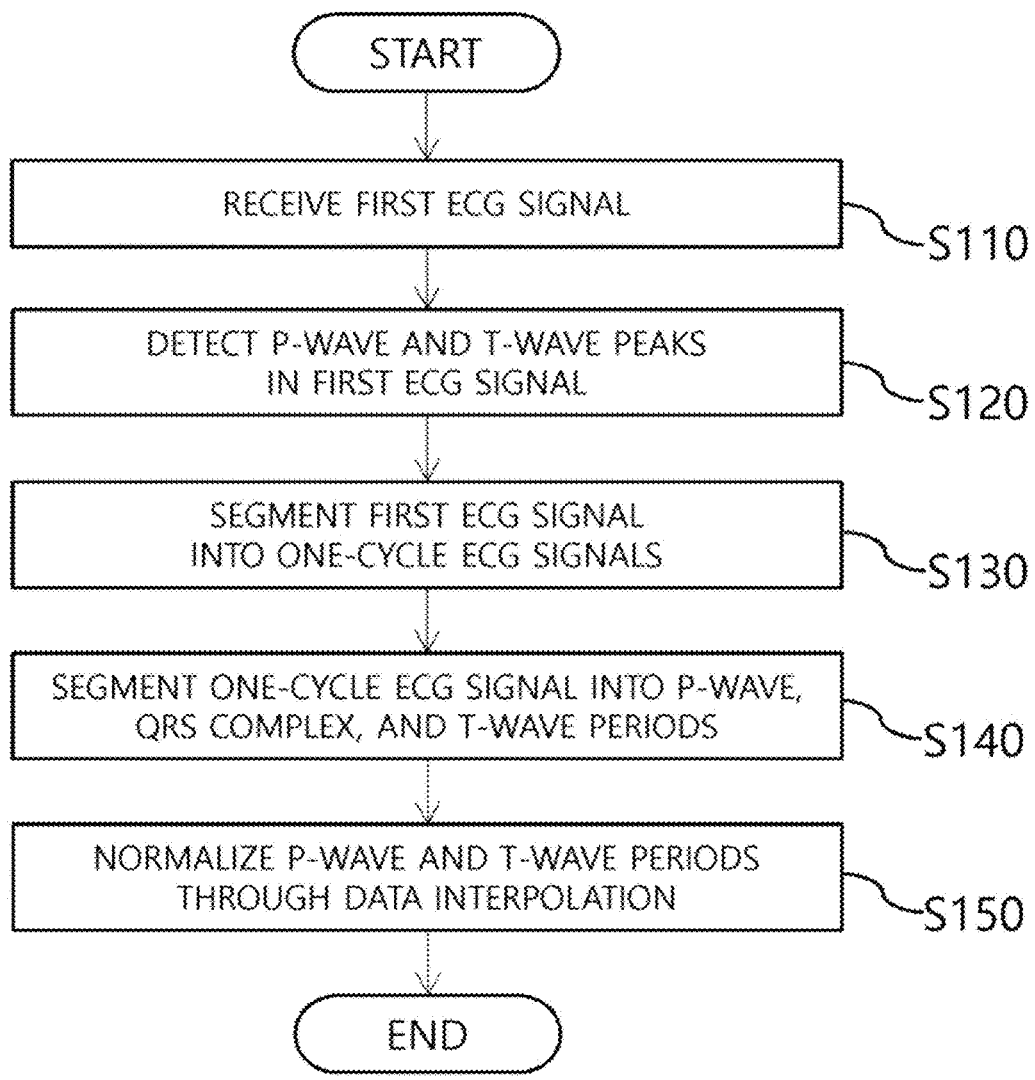
FIG. 1 is a flowchart illustrating a method of normalizing a tachycardia electrocardiogram (ECG) on the basis of P-wave and T-wave data interpolation according to an exemplary embodiment of the present invention.

Specific structural or functional descriptions of exemplary embodiments of the present invention disclosed in this specification or the application are merely illustrated to describe the exemplary embodiments of the present invention. Embodiments of the present invention may be implemented in various forms and should not be construed as being limited to the embodiments described in this specification or application.

The exemplary embodiments of the present invention may be modified in various ways and may have several forms, and thus specific exemplary embodiments are illustrated in the drawings and are described in detail in this specification or application. However, this is not intended to limit an embodiment according to the concept of the present invention to a specific disclosure, and it is to be understood that the embodiment encompasses all changes, equivalents, and substitutions which fall within the spirit and technical scope of the present invention.

The terms "first," "second," and/or the like may be used only to distinguish one element from another. In other words, the elements are not limited to the terms.

The term "include" indicates the presence of a stated element, characteristic, and step and does not exclude the presence of one or more other elements, characteristics, steps, and equivalents thereof.

The singular includes the plural unless the context specifically indicates otherwise. In other words, an element or the like mentioned herein may denote the presence of addition of one or more other elements or the like.

All terms used herein, including technical or scientific terms, have the same meanings as those typically understood by those of ordinary skill in the technical field to which the present invention pertains unless otherwise defined.

In other words, terms, such as those defined in common dictionaries, should be construed as having the same meanings as terms in the context of related technology and should not be construed as having ideal or excessively formal meanings unless clearly defined herein.

Hereinafter, exemplary embodiments of the present invention will be described in detail with reference to the accompanying drawings.

FIG. 1 is a flowchart illustrating a method of normalizing a tachycardia electrocardiogram (ECG) on the basis of P-wave and T-wave data interpolation according to an exemplary embodiment of the present invention.

Referring to FIG. 1, the method of normalizing a tachycardia ECG on the basis of P-wave and T-wave data interpolation according to an exemplary embodiment of the present invention may include operation S110 of receiving a first ECG signal from a subject, operation S120 of detecting P-wave and T-wave peaks in the received first ECG signal, operation S130 of segmenting the received first ECG signal into one-cycle ECG signals on the basis of the detected P-wave and T-wave peaks, operation S140 of segmenting the one-cycle ECG signals into a P-wave period, a QRS complex period, and a T-wave period, and operation S150 of normalizing the segmented P-wave and T-wave periods through data interpolation.

In operations S110 to S150 of the method of normalizing a tachycardia ECG on the basis of P-wave and T-wave data interpolation according to an exemplary embodiment of the present invention, operation S110 may be performed by a receiver provided in an electronic device, and operations S120 to S150 may be performed by a controller provided in the electronic device.

In operation S110 of receiving a first ECG signal from a subject, the first ECG signal of the subject whose ECG will be measured, that is, a post-exercise tachycardia ECG signal of the subject, is received.

According to an exemplary embodiment, the method of normalizing a tachycardia ECG on the basis of P-wave and T-wave data interpolation may further include an operation of receiving a second ECG signal from the subject before operation S110. This operation may also be performed by the receiver of the electronic device.

In order to improve recognition performance, it is necessary to normalize cycles of the first ECG signal which corresponds to a tachycardia ECG into general pre-exercise cycles of the second ECG signal. Consequently, after the second ECG signal is received, the second ECG signal may be stored as data, and cycles, P wave, QRS complex, T wave periods, etc. of the second ECG signal may be measured. In other words, the second ECG signal, cycles thereof, etc. are measured and stored or used as registration data, and the first ECG signal is used as recognition data.

In the operation S120 of detecting P-wave and T-wave peaks in the received first ECG signal, the positions of P-wave and T-wave peaks are detected in the first ECG signal measured from the subject.

Figure 2:
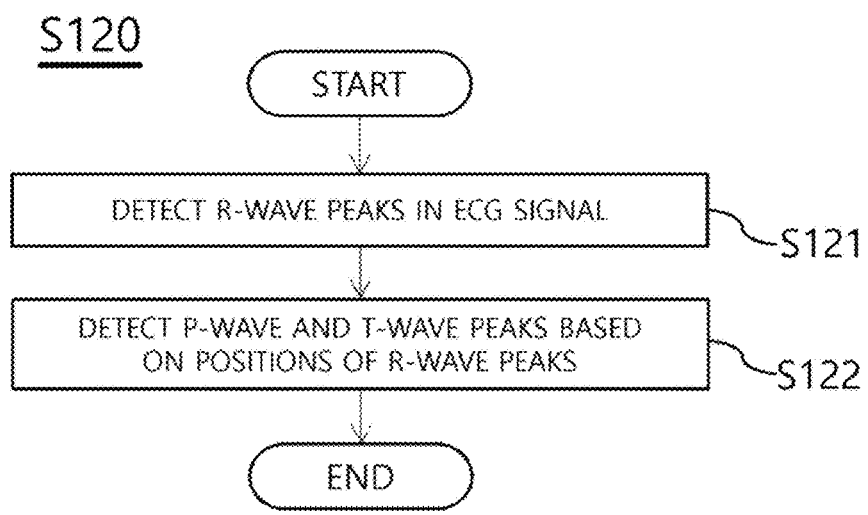
FIG. 2 is a flowchart of operation S120 of the method of normalizing a tachycardia ECG on the basis of P-wave and T-wave data interpolation according to an exemplary embodiment of the present invention.

FIG. 2 is a flowchart of operation S120 of the method of normalizing a tachycardia ECG on the basis of P-wave and T-wave data interpolation according to an exemplary embodiment of the present invention.

Referring to FIG. 2, operation S120 may include operation S121 of detecting R-wave peaks in the received ECG signal and operation S122 of detecting P-wave and T-wave peaks in the received ECG signal on the basis of the detected R-wave peaks.

In operation S121 of detecting R-wave peaks in the received ECG signal, R-wave peaks included in QRS complexes are detected in the received first ECG signal.

Figure 3A:
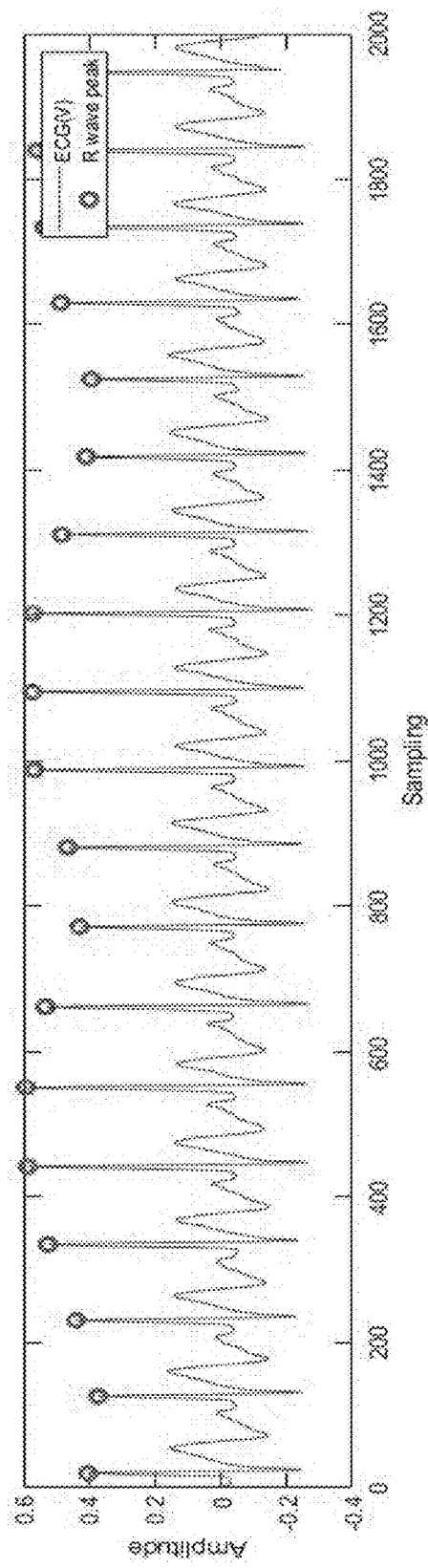
FIG. 3A is an image showing R-wave peaks detected in an input ECG signal in the method of normalizing a tachycardia ECG on the basis of P-wave and T-wave data interpolation according to an exemplary embodiment of the present invention.

FIG. 3A is an image showing R-wave peaks detected in an input ECG signal in the method of normalizing a tachycardia ECG on the basis of P-wave and T-wave data interpolation according to an exemplary embodiment of the present invention.

Referring to FIG. 3A, it is possible to see that R-wave peaks are marked in QRS complex periods.

According to an exemplary embodiment, R-wave peaks may be detected by using the Pan-Tompkins algorithm. The Pan-Tompkins algorithm is an algorithm for detecting R-wave peaks with a threshold.

In operation S122 of detecting P-wave and T-wave peaks in the received ECG signal on the basis of the detected R-wave peaks, P-wave and T-wave peaks are detected on the basis of the R-wave peaks detected in operation S121.

P-wave peaks may be detected in peak portions of preset periods on the left sides of the detected R-wave peaks.

According to an exemplary embodiment, a P-wave peak may be a peak portion in the period between 0.15 s and 0.05 s on the left side of an R-wave peak.

T-wave peaks may be detected in peak portions of preset periods on the right sides of the detected R-wave peaks.

According to an exemplary embodiment, a T-wave peak may be a peak portion in the period between 0.05 s and 0.3 s on the right side of an R-wave peak.

Figure 3B:
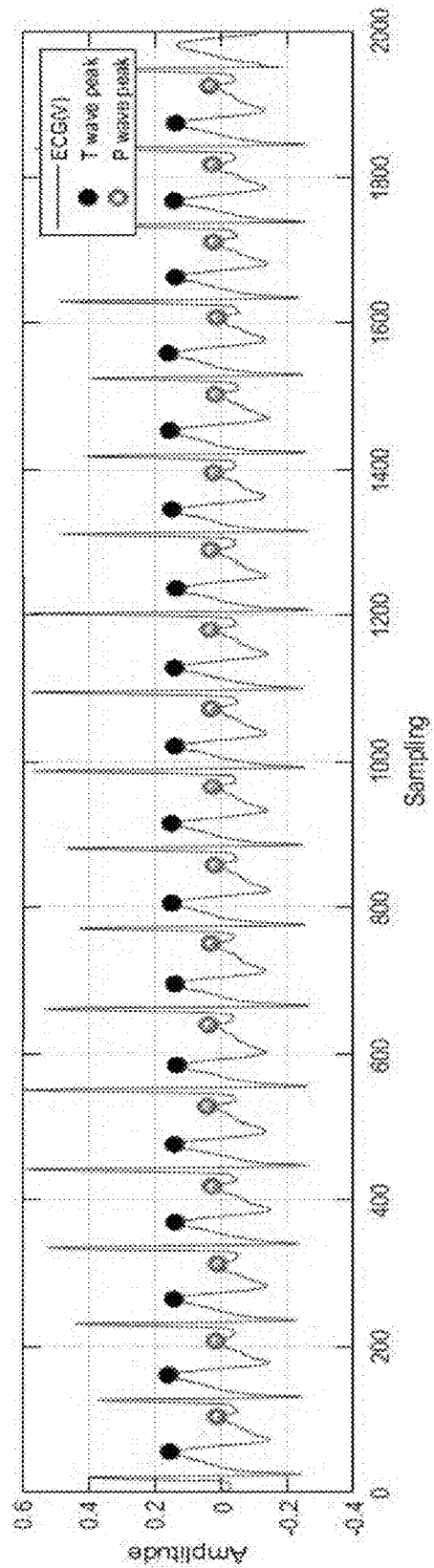
FIG. 3B is an image showing P-wave and T-wave peaks detected in an input ECG signal in the method of normalizing a tachycardia ECG on the basis of P-wave and T-wave data interpolation according to an exemplary embodiment of the present invention.

FIG. 3B is an image showing P-wave and T-wave peaks detected in an input ECG signal in the method of normalizing a tachycardia ECG on the basis of P-wave and T-wave data interpolation according to an exemplary embodiment of the present invention.

Referring to FIG. 3B, it is possible to see that P-wave peaks are on the left sides of detected R-wave peaks and T-wave peaks are on the right sides of the detected R-wave peaks.

In operation S130 of dividing the received first ECG signal into one-cycle ECG signals on the basis of the detected P-wave and T-wave peaks, the received first ECG signal is divided into one-cycle ECG signals, which are minimum units of the first ECG signal, on the basis of the positions of the P-wave and T-wave peaks detected in operation S120.

A one-cycle ECG signal may be segmented on the basis of a preset position on the left side of a detected P-wave peak and a preset position on the right side of the detected T-wave peak.

According to an exemplary embodiment, a one-cycle ECG signal may be segmented on the basis of a 0.1 s position on the left side of a P-wave peak and a 0.25 s position on the right side of a T-wave peak.

Figure 4:
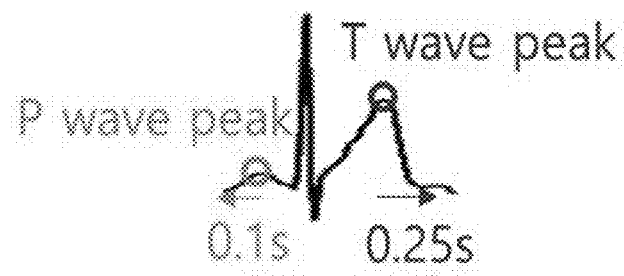
FIG. 4 is an image showing a one-cycle ECG signal segmented from an input ECG signal in the method of normalizing a tachycardia ECG on the basis of P-wave and T-wave data interpolation according to an exemplary embodiment of the present invention.

FIG. 4 is an image showing a one-cycle ECG signal segmented from a received ECG signal in the method of normalizing a tachycardia ECG on the basis of P-wave and T-wave data interpolation according to an exemplary embodiment of the present invention.

Referring to FIG. 4, it is possible to see that a one-cycle ECG signal is segmented on the basis of a 0.1 s position on the left side of a detected P-wave peak and a 0.25 s position on the right side of a detected T-wave peak.

In operation S140 of dividing the one-cycle ECG signals into a P-wave period, a QRS complex period, and a T-wave period, the one-cycle ECG signals segmented in operation S130 are divided into a P-wave period, a QRS complex period, and a T-wave period.

According to an exemplary embodiment, a QRS complex period may be segmented on the basis of preset positions on the left and right sides of a detected R-wave peak. For example, a QRS complex period may be segmented to have a period from a 0.05 s position on the left side of an R-wave peak to a 0.05 s position on the right side of the R-wave peak.

In a one-cycle ECG signal, a P-wave period may be on the left side of a QRS complex period, and a T-wave period may be on the right side of the QRS complex period.

Figure 5:
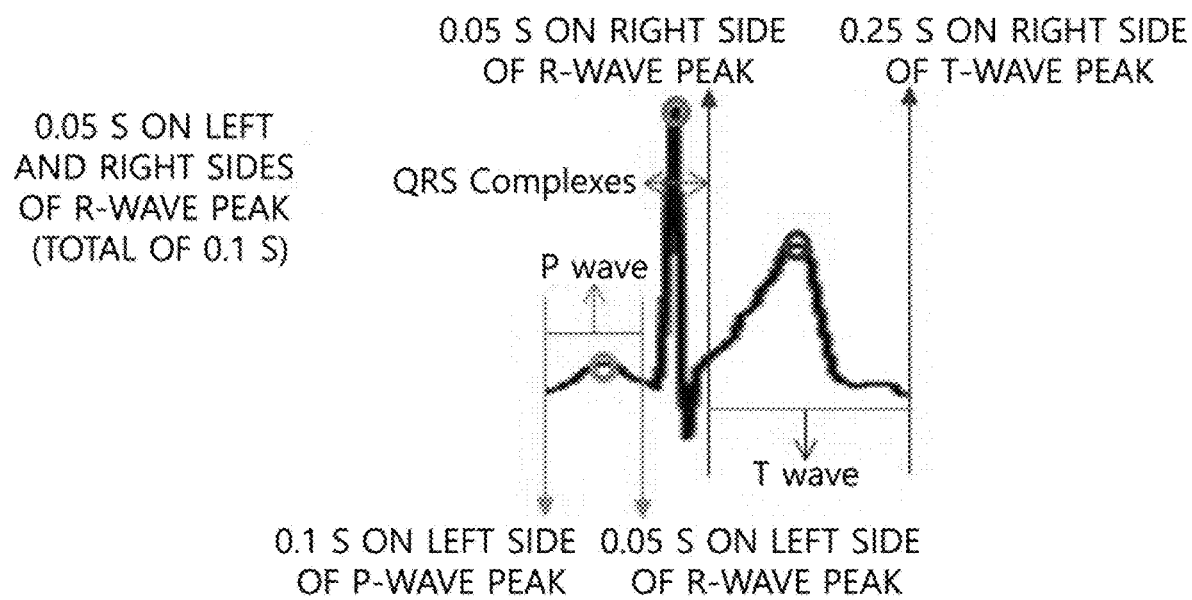
FIG. 5 is an image showing a one-cycle ECG signal divided into a P-wave period, a QRS complex period, and a T-wave period in the method of normalizing a tachycardia ECG on the basis of P-wave and T-wave data interpolation according to an exemplary embodiment of the present invention.

FIG. 5 is an image showing a one-cycle ECG signal divided into a P-wave period, a QRS complex period, and a T-wave period in the method of normalizing a tachycardia ECG on the basis of P-wave and T-wave data interpolation according to an exemplary embodiment of the present invention. In FIG. 5, the one-cycle ECG signal segmented in FIG. 4 is segmented into a P-wave period, a QRS complex period, and a T-wave period.

Referring to FIG. 5, the QRS complex period is segmented to have 0.05 s on the left side of the R-wave peak and 0.05 s on the right side as a total period of 0.1 s. The P-wave period is from a 0.05 s position on the left side of the QRS complex period, that is, the R-wave peak, to a 0.1 s position on the left side of the P-wave peak, and the T-wave period is from a 0.05 s position on the right side of the QRS complex period, that is, the R-wave peak, to a 0.25 s position on the right side of the T-wave peak.

Figure 6:
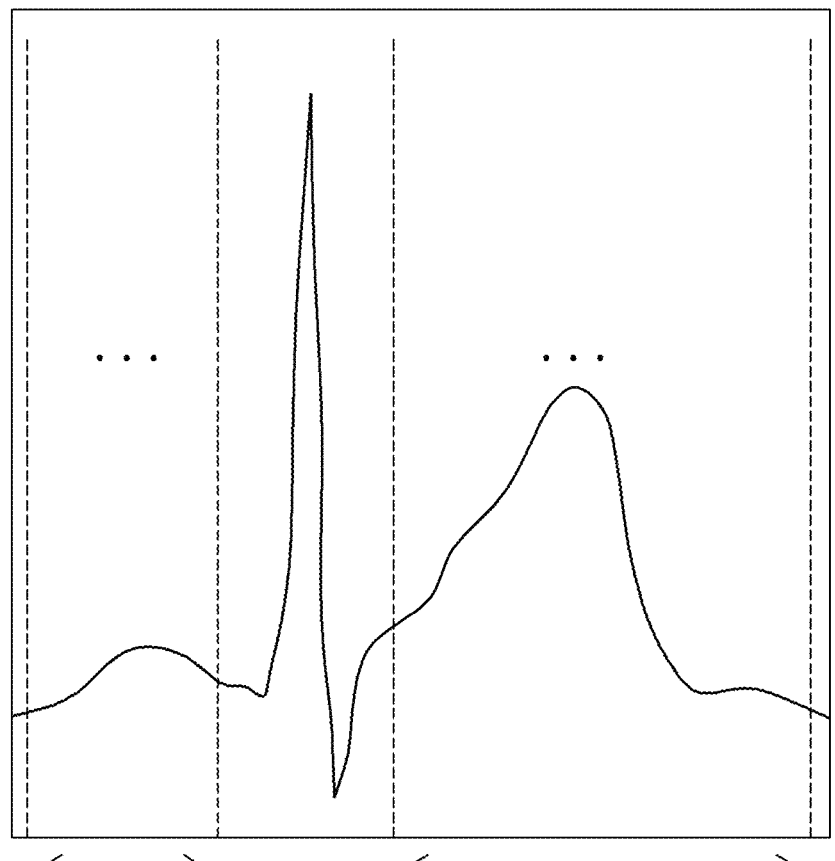
FIG. 6 is an image showing a period undergoing a normalization process and a period not undergoing a normalization process in the method of normalizing a tachycardia ECG on the basis of P-wave and T-wave data interpolation according to an exemplary embodiment of the present invention.

FIG. 6 is an image showing a period undergoing a normalization process and a period not undergoing a normalization process in the method of normalizing a tachycardia ECG on the basis of P-wave and T-wave data interpolation according to an exemplary embodiment of the present invention.

Referring to FIG. 6, it is possible to see that a QRS complex period among segmented P-wave, QRS complex, and T-wave periods is excluded from a data interpolation process. In other words, only the P-wave and T-wave periods are normalized through data interpolation, and the QRS complex period does not undergo a normalization process.

The QRS complex period includes unique individual bio-information and thus is not affected by tachycardia. To prevent distortion or period deviation of the ECG, the QRS complex period is excluded from the normalization process based on data interpolation. Accordingly, it is possible to solve the problem that the positions of QRS complex periods are not fixed in a related normalization technology.

In operation S150 of normalizing the segmented P-wave and T-wave periods through data interpolation, the P-wave and T-wave periods segmented in operation S140 are normalized according to cycles of the second ECG signal.

After the second ECG signal is received to normalize the first ECG signal according to cycles of the second ECG signal, P-wave periods and T-wave periods of the second ECG signal may be set. For example, P-wave periods may be set to 0.2 s, and T-wave periods may be set to 0.45 s.

According to an exemplary embodiment, when the product of a sampling rate and P-wave periods of the first ECG signal and the product of the sampling rate and T-wave periods of the first ECG signal are less than the number of pieces of P-wave data and the number of pieces of T-wave data, respectively, the P-wave and T-wave periods of the first ECG signal may be normalized through data interpolation.

Here, the sampling rate is the number of sampling operations per unit time obtained from a continuous signal to generate a discrete signal.

For example, when the sampling rate is 200 Hz and the P-wave periods of the second ECG signal are 0.2 s, the number of pieces of data of the P-wave period is 200 Hz×0.2 s=40. When the sampling rate is 200 Hz and the T-wave period of the second ECG signal is 0.45 s, the number of pieces of data of the T-wave period is 200 Hz×0.45 s=90. In this case, when the number of pieces of P-wave period data of the first ECG signal is less than 40 and the number of pieces of T-wave period data of the first ECG signal is less than 90, the P-wave periods and the T-wave periods are normalized through data interpolation.

The number of pieces of P-wave period data and the number of pieces of T-wave period data may be increased or decreased according to a change in sampling rate. For example, assuming that P-wave periods are 0.2 s and T-wave periods are 0.45 s as described above, when the sampling rate is 400 Hz, the number of pieces of P-wave period data is 80, and the number of pieces of T-wave period data is 180. When the sampling rate is 100 Hz, the number of pieces of P-wave period data is 20, and the number of pieces of T-wave period data is 45.

In other words, the first ECG signal is generated at shorter intervals than the second ECG signal due to tachycardia after exercise, and thus P-wave and T-wave periods narrow. For this reason, the number of pieces of data is decreased compared to that of the pre-exercise ECG. Consequently, only when the sizes of the P-wave and T-wave periods of the first ECG signal are respectively smaller than the sizes of the P-wave and T-wave periods of the second ECG signal, are the P-wave and T-wave periods normalized through data interpolation.

Figure 7:
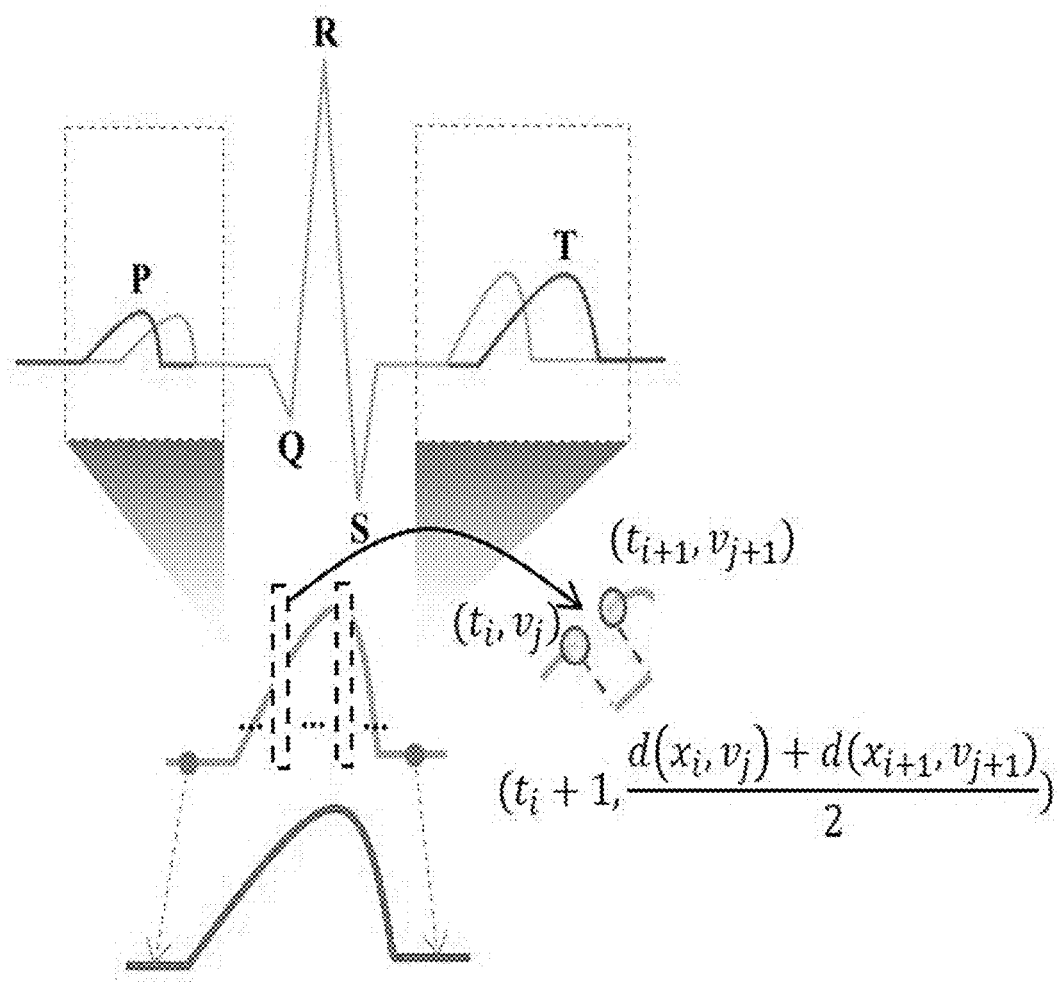
FIG. 7 is an image showing a process of normalizing a P-wave period and a T-wave period through data interpolation in the method of normalizing a tachycardia ECG on the basis of P-wave and T-wave data interpolation according to an exemplary embodiment of the present invention.

FIG. 7 is an image showing a process of normalizing a P-wave period and a T-wave period through data interpolation in the method of normalizing a tachycardia ECG on the basis of P-wave and T-wave data interpolation according to an exemplary embodiment of the present invention.

Referring to FIG. 7, it is possible to see that P-wave and T-wave periods of a first ECG signal having shorter intervals are normalized according to a cycle of a second ECG signal.

A process of normalizing P-wave and T-wave periods on the basis of data interpolation may be defined by the following equation.

$$d_n = r_s \times t_n$$
$$d_r = r_s \times t_r$$
$$N_i = d_n - d_r$$
$$X_i = Int\left(\frac{d_r}{N_i + 1}\right) \times i, i = 1, \ldots, N_i$$
$$V_t = \frac{v_t(x_t) + v_{t+1}(x_{t+1})}{2}$$

[Equation 1]

Here, $d_n$ is the number of pieces of P-wave or T-wave period data after normalization, that is, the number of pieces of P-wave or T-wave period data of the second ECG signal. $r_s$ is the sampling rate, and to is the time of the P-wave or T-wave periods after normalization, that is, the time of the P-wave or T-wave periods of the second ECG signal. $d_r$ is the number of pieces of P-wave or T-wave period data of the first ECG signal before normalization, $t_r$ is the time of the P-wave or T-wave periods of the first ECG signal before normalization, $N_i$ is the number of pieces of data to be normalized, $x_i$ is a data interpolation position, Int is an integer conversion function, $v_i$ is a voltage value at the position $x_i$, and $V_t$ is a voltage value after normalization.

In other words, P-wave period data or T-wave period data is normalized according to cycles of the second ECG signal by interpolating as much P-wave period data or T-wave period data as a difference in the number pieces of P-wave period or T-wave period data between the received first ECG signal and the pre-exercise second ECG signal. A P-wave and T-wave period normalization process is performed through linear interpolation of data based on Equation 1. Referring to FIG. 7, a voltage value after linear interpolation of data is given as the fifth equation of Equation 1.

Since linear interpolation of data is selectively applied to only P-wave and T-wave periods, it is possible to minimize distortion of P-wave, QRS complex, and T-wave periods and fix the positions of QRS complexes.

According to an exemplary embodiment, the method of normalizing a tachycardia ECG on the basis of P-wave and T-wave data interpolation may further include an operation of combining the interpolated P-wave and T-wave periods with the QRS complex period.

In other words, the P-wave and T-wave periods, of which data has been interpolated, are combined with the QRS complex period which has not undergone a data interpolation process so that a normalization process in which the P-wave and T-wave periods are normalized according to cycles of the second ECG signal is finally finished. This process may also be performed by the controller provided in the electronic device.

Figure 8A:
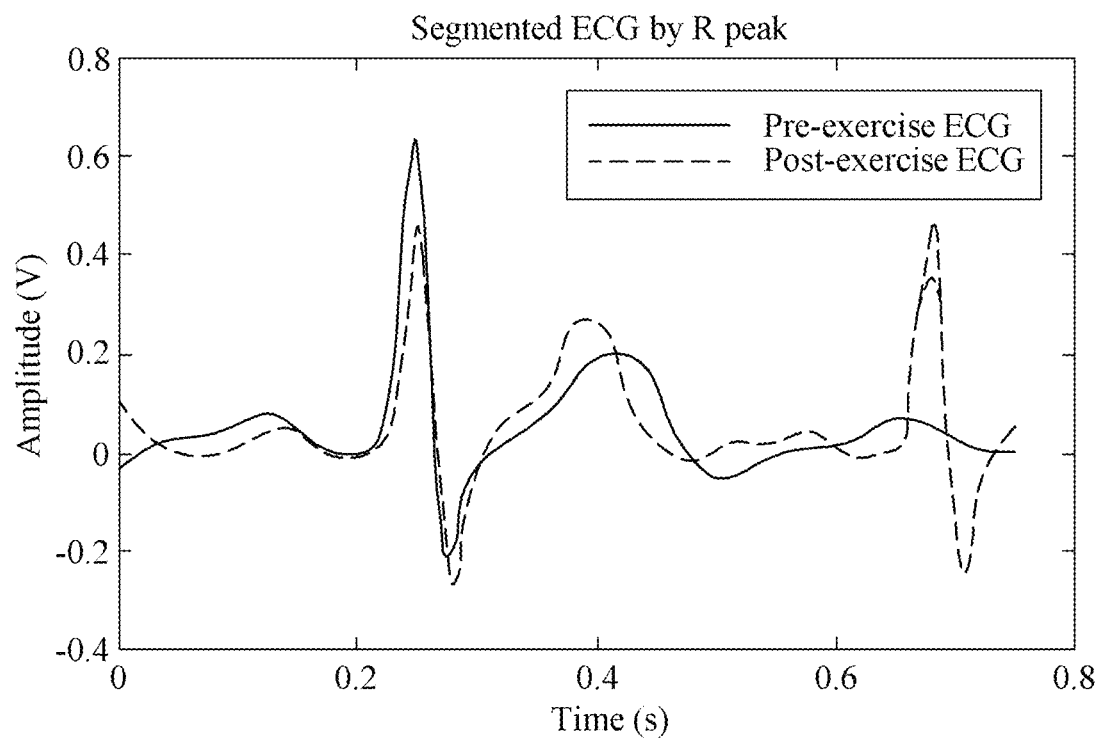
FIGS. 8A and 8B are graphs showing a first ECG signal before and after normalization and a second ECG signal in the method of normalizing a tachycardia ECG on the basis of P-wave and T-wave data interpolation according to an exemplary embodiment of the present invention.
Figure 8B:
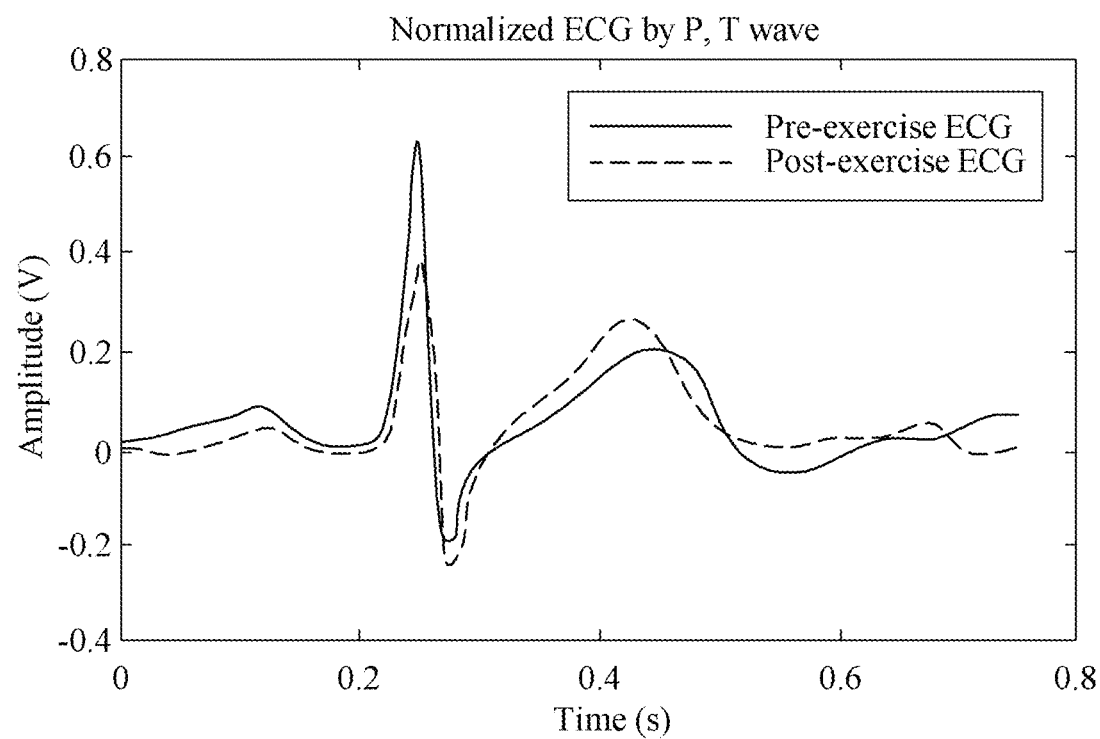

FIGS. 8A and 8B are graphs showing a first ECG signal before and after normalization and a second ECG signal after exercise in the method of normalizing a tachycardia ECG on the basis of P-wave and T-wave data interpolation according to an exemplary embodiment of the present invention. FIG. 8A shows P waves, QRS complexes, and T waves of a first ECG signal before normalization and P waves, QRS complexes, and T waves of a second ECG signal, and FIG. 8B shows P waves, QRS complexes, and T waves of the first ECG signal after normalization and P waves, QRS complexes, and T waves of the second ECG signal.

Referring to FIGS. 8A and 8B, it is possible to see that P-wave and T-wave periods of the first ECG signal, which is a post-exercise ECG signal, are normalized according to cycles of the second ECG signal, which is a general pre-exercise ECG signal, through data interpolation-based normalization.

The method of normalizing a tachycardia ECG on the basis of P-wave and T-wave data interpolation according to an exemplary embodiment of the present invention may be implemented in the form of a computer-readable recording medium which stores a program for executing the method in a computer. The computer-readable recording medium may be any available medium accessible by a computer and may include all of volatile or non-volatile media and removable or non-removable media. Also, the computer-readable recording medium may include a computer storage medium. The computer storage medium may include all of volatile or non-volatile and removable or non-removable media that are implemented by any method or technology to store information such as computer-readable instructions, data structures, program modules, or other data.

Exemplary modules, operations, or a combination thereof related to exemplary embodiments described herein may be implemented by electronic hardware (a digital design made through coding or the like), software (various applications including a program instruction), or a combination thereof. Implementation as any form of the hardware and/or software may be changed according to design limitations imposed on user equipment.

One or more elements described herein may be stored in a memory as a computer program instruction, and a digital signal processor may execute the method described herein through the computer program instruction. Connection examples between elements specified in the drawings appended hereto are only exemplary. At least some of the elements may be omitted, and on the other hand, elements may be further included in addition to the elements.

Experimental Example

Pre-exercise, mid-exercise, and post-exercise ECGs of 20 subjects were input, and ECG similarity according to whether normalization was performed was measured by applying the method of normalizing a tachycardia ECG on the basis of P-wave and T-wave data interpolation according to an exemplary embodiment of the present invention to ECGs in a general state, pre-exercise and mid-exercise states, mid-exercise and post-exercise states, and pre-exercise and post-exercise states.

FIG. 9 is a table showing results of measuring similarity in the experimental example.

As shown in FIG. 9, ECG cycles and ECG similarity according to whether normalization was performed were measured through a Euclidean distance value, and a similarity variation was measured through an overall average of the 20 subjects.

As experimental results, when the method of normalizing a tachycardia ECG on the basis of P-wave and T-wave data interpolation according to an exemplary embodiment of the present invention was used, a similarity was increased by 1.2% in the general state, increased by 4.8% in the pre-exercise and mid-exercise states, increased by 18.1% in the mid-exercise and post-exercise states, and increased by 23.5% in the pre-exercise and post-exercise states compared to that of a case in which the normalization method is not used.

Therefore, when the normalization method according to an exemplary embodiment of the present invention is used, distortion of P-wave, QRS complex, and T-wave periods is minimized, and QRS complex periods are not changed. Consequently, a similarity with a pre-exercise ECG can be increased after normalization, and ECG recognition performance can be improved.

With the method of normalizing a tachycardia ECG on the basis of P-wave and T-wave data interpolation according to an exemplary embodiment of the present invention, it is possible to make a post-exercise tachycardia ECG correspond to a pre-exercise ECG cycle by interpolating data of P waves and T waves of the tachycardia ECG.

Also, the method of normalizing a tachycardia ECG on the basis of P-wave and T-wave data interpolation according to an exemplary embodiment of the present invention does not distort P waves, QRS complexes, and T waves.

Further, in the method of normalizing a tachycardia ECG on the basis of P-wave and T-wave data interpolation according to an exemplary embodiment of the present invention, the positions of QRS complex periods are fixed even after normalization.

Effects of the present invention are not limited to those mentioned above, and other effects which have not been mentioned will be clearly understood by those of ordinary skill in the art from the above descriptions.

The above descriptions are merely examples of the technical spirit of the present invention, and those of ordinary skill in the technical field to which the present invention pertains can make various modifications and alterations without departing from the fundamental features of the present invention. Therefore, the embodiments disclosed in the present invention are intended to illustrate but not to limit the scope of the technical spirit of the present invention, and the scope of the present invention is not limited by the embodiments. The scope of the present invention shall be construed on the basis of the following claims in such a manner that all of the technical spirits within the scope equivalent to the claims belong to the present invention.

What is claimed is:

1. A method of normalizing a tachycardia electrocardiogram (ECG) on the basis of P-wave and T-wave data interpolation, the method comprising:
    (a) receiving a first ECG signal from a subject;
    (b) detecting P-wave and T-wave peaks in the received first ECG signal;
    (c) segmenting the received first ECG signal into a one-cycle ECG signal on the basis of the detected P-wave and T-wave peaks;
    (d) segmenting the one-cycle ECG signal into a P-wave period, a QRS complex period, and a T-wave period; and
    (e) normalizing the segmented P-wave and T-wave periods through data interpolation.

2. The method of claim 1, further comprising, before operation (a), receiving a second ECG signal from the subject.

3. The method of claim 2, wherein operation (e) comprises normalizing the segmented P-wave and T-wave periods according to a cycle of the second ECG signal through data interpolation.

4. The method of claim 1, wherein operation (b) comprises:
    (b-1) detecting an R-wave peak in the received first ECG signal; and
    (b-2) detecting the P-wave and T-wave peaks in the received first ECG signal on the basis of a position of the detected R-wave peak.

5. The method of claim 4, wherein operation (b-1) comprises detecting the R-wave peak by using a Pan-Tomkins algorithm.

6. The method of claim 4, wherein operation (b-2) comprises detecting a peak in a preset period on a left side of the R-wave peak as the P-wave peak and detecting a peak in a preset period on a right side of the R-wave peak as the T-wave peak.

7. The method of claim 1, wherein operation (c) comprises segmenting the received first ECG signal into the one-cycle ECG signal on the basis of a preset position on a left side of the P-wave peak and a preset position on a right side of the T-wave peak.

8. The method of claim 4, wherein operation (d) comprises segmenting the one-cycle ECG signal into the QRS complex period on the basis of preset positions on a left side and a right side of the R-wave peak.

9. The method of claim 2, wherein operation (e) comprises, when sizes of the P-wave and T-wave periods of the first ECG signal are respectively smaller than sizes of P-wave and T-wave periods of the second ECG signal, normalizing the P-wave and T-wave periods through data interpolation.

10. The method of claim 1, further comprising, after operation (e), combining the P-wave and T-wave periods, of which data has been interpolated, with the QRS complex period.

11. A computer-readable recording medium in which a program for executing the method according to claim 1 in a computer is recorded.

\* \* \* \* \*